(12) United States Patent
Marseille

(10) Patent No.: US 8,882,695 B2
(45) Date of Patent: Nov. 11, 2014

(54) ARRANGEMENT WITH A BLOOD PUMP AND A GAS EXCHANGER FOR EXTRACORPOREAL MEMBRANE OXYGENATION

(75) Inventor: Oliver Marseille, Aachen (DE)

(73) Assignee: Mecora Medizintechnik GmbH (DE)

( * ) Notice: Subject to any disclaimer, the term of this patent is extended or adjusted under 35 U.S.C. 154(b) by 0 days.

(21) Appl. No.: 13/521,857

(22) PCT Filed: Jan. 10, 2011

(86) PCT No.: PCT/DE2011/000009
§ 371 (c)(1),
(2), (4) Date: Aug. 29, 2012

(87) PCT Pub. No.: WO2011/085714
PCT Pub. Date: Jul. 21, 2011

(65) Prior Publication Data
US 2013/0004369 A1    Jan. 3, 2013

Related U.S. Application Data

(60) Provisional application No. 61/335,881, filed on Jan. 13, 2010.

(30) Foreign Application Priority Data

Jan. 13, 2010   (DE) .......................... 10 2010 004 600

(51) Int. Cl.
*A61M 37/00*   (2006.01)
*A61M 1/10*    (2006.01)
*A61M 1/16*    (2006.01)

(52) U.S. Cl.
CPC ............. *A61M 1/1698* (2013.01); *A61M 1/106* (2013.01); *A61M 1/1006* (2013.01)
USPC .......................................................... 604/6.14

(58) Field of Classification Search
CPC .. A61M 1/106; A61M 1/1678; A61M 1/1698
USPC ............................. 422/44–48; 604/4.01–6.16
See application file for complete search history.

(56) References Cited

U.S. PATENT DOCUMENTS 3,639,084 A * 2/1972 Goldhaber .................... 417/394
4,094,792 A * 6/1978 Bentley ..................... 210/321.67

(Continued)

FOREIGN PATENT DOCUMENTS

| CN | 1 528 472 | 9/2004 |
| DE | 10 2007 010112 | 9/2009 |
| WO | WO 2004/043517 | 5/2004 |

(Continued)

OTHER PUBLICATIONS

International Search Report of PCT/DE2011/000009, date of mailing May 31, 2011.
International Preliminary Report on Patentability of PCT/DE2011/000009, Jul. 2012.

*Primary Examiner* — Philip R Wiest
*Assistant Examiner* — Benjamin Klein
(74) *Attorney, Agent, or Firm* — Wilson Sonsini Goodrich & Rosati

(57) ABSTRACT

The invention relates to an arrangement having a blood pump and a gas exchanger for extracorporeal membrane oxygenation. According to the invention, the blood pump is designed as a pulsatile blood pump and is arranged with the gas exchanger in the same housing. The pulsatile blood pump and the gas exchanger are preferably connected to the same gas source so that the blood pump can be pneumatically driven. The novel ECMO system has a simple design, is flexible, and in particular can be used directly on the patient.

19 Claims, 3 Drawing Sheets

(56) References Cited

Figure 1:
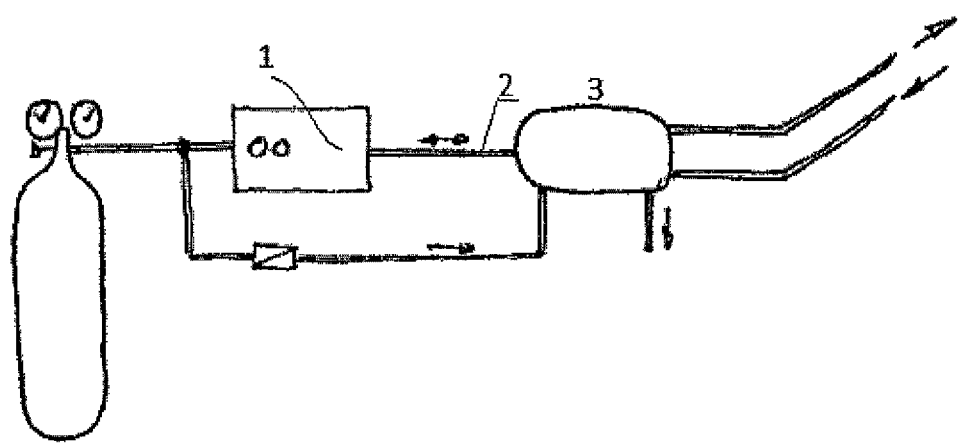

U.S. PATENT DOCUMENTS 4,116,589 A * 9/1978 Rishton .................. 417/384
4,182,653 A * 1/1980 Bellhouse ................ 435/2
5,965,433 A * 10/1999 Gardetto et al. ......... 422/48
6,312,647 B1 * 11/2001 Spears .................... 422/48

2010/0106072 A1    4/2010 Kashefi-Khorasani et al.

FOREIGN PATENT DOCUMENTS

WO    WO 2005/028002    3/2005
WO    WO 2009/110652    9/2009

* cited by examiner

ARRANGEMENT WITH A BLOOD PUMP AND A GAS EXCHANGER FOR EXTRACORPOREAL MEMBRANE OXYGENATION

CROSS REFERENCE TO RELATED APPLICATIONS

This application is the National Stage of PCT/DE2011/000009 filed on Jan. 10, 2011, which claims priority under 35 U.S.C. §119 of German Application No. 10 2010 004 600.0 filed on Jan. 13, 2010, and under 35 U.S.C. §119(e) of U.S. Provisional Application Ser. No. 61/335,881 filed on Jan 13, 2010, the disclosures of which are incorporated by reference. The international application under PCT article 21(2) was not published in English.

The invention concerns an arrangement with a blood pump and a gas exchanger for extracorporeal membrane oxygenation.

The heart, as the central organ of the circulatory system, is a hollow muscle with two chambers, which pumps the blood in circulation by contraction and relaxation. With its left chamber (left ventricle) the blood is pumped through the arterial blood vessels of the large circulation to the blood capillaries of the periphery of the body. The blood returns to the right chamber of the heart (right ventricle) through the venous blood vessels. From there it is pumped through the pulmonary arteries in the pulmonary circulation (small circulation) to the lungs and returns via the pulmonary veins to the left ventricle. The small circulation is located very high in the chest.

In cardiac disease patients can reach a position in which an artificial circulation support system becomes the only possible, and therefore life-sustaining, treatment. While in cardiac cardiac support systems which replace the pump function of the right, left or both sides of the heart a direct connection to blood vessels in the chest must be produced, the ECMO systems (extracorporeal membrane oxygenation), which work by taking over and/or supporting the entire function of the internal circulation, i.e. of the right and left chamber and the lungs, enable a simpler connection capability.

ECMO systems can be connected to peripheral blood vessels. This makes so-called cannulation easier and safer and means that it can also be used outside of specialist clinics. In addition, in an acute emergency an ECMO system can be cannulated considerably faster, thereby supplying the patient with the vital life support.

ECMO systems consist of a blood pump and an oxygenator, which supports the lung function and thus reduces the CO2 in the blood and allows the O2 to accumulate.

ECMO systems can pump the blood in parallel to the internal circulation, by the blood being taken from a vein (venously) and supplied to an artery (arterially). In this case the pump pumps the blood via the arterio-venous pressure difference and thus enables, in parallel with the heart, blood flow in the periphery of the body and hence to the vital organs.

In cases of pulmonary disease, the use of ECMO systems may also be the only life-sustaining treatment option. If the lungs can no longer adequately fulfil their function even by artificial respiration, all other organs suffer due to the absence of CO2 reduction and O2 supply and the patient reaches a life-threatening situation.

In the treatment of lung diseases using ECMO systems these can also be connected to the patient intravenously, since only the function of the lungs is taken over.

Current ECMO systems include oxygenators, in which the gas exchange takes place by means of membrane fiber bundles. The transport of gas takes place, as is also the case in the lungs, via the concentration gradient between the blood and the oxygen which is supplied to the oxygenator. Oxygenators currently used in ECMO systems are borrowed from heart-lung machines, such as are used in operations on the heart during cardiac surgery.

The pumps of the ECMO systems are also borrowed from the heart-lung machine. Centrifugal pumps with a radial or diagonal design are used, which are driven via an electric motor.

In recent times, ECMO systems have been developed which combine such centrifugal pumps and oxygenators and therefore enable more compact systems with lower filling volumes (priming volumes). These systems are stationary in use and cannot be operated directly on the patient, since they are location-dependent and need to be fixed in appropriate, rigid mountings.

In the case of stable cardiac function where only one lung support is required, a system is also used in which the pressure gradient between the arterial and venous vessels is exploited to permeate the oxygenator. These systems therefore operate without a pump.

Due to the relatively large surface extraneous to the body, existing ECMO systems may only be used for limited periods of time, and accompanied by the use of anticoagulant drugs. In spite of the drugs, the systems tend to lead to the formation of thrombi and must be frequently replaced.

They are complicated to operate and normally require specialist personnel familiar with operating heart-lung machines.

The control consoles of the systems used are relatively complex and expensive.

Even if ECMO systems are now used for patient transport, the drive units are relatively heavy because for transport purposes they require a non-mains power supply to allow standalone operation.

In the systems without a pump problems can occur if the cardiac function deteriorates during the treatment.

The object of the invention is to further develop an arrangement with a blood pump and a gas exchanger for extracorporeal membrane oxygenation.

This object is achieved with an arrangement of generic kind, in which the blood pump is implemented as a pulsatile blood pump and arranged with the gas exchanger in the same housing.

A structure is preferably selected in which the blood inlet line is directly connected to the pulsatile blood pump without a reservoir. A reservoir, which is usually found in heart-lung machines, is unnecessary since due to the pulsatile blood pump, limited suction pressures cannot lead to the critical suction in the blood vessel.

Furthermore, an arrangement is proposed in which the blood outlet line is directly connected to the gas exchanger. A filter between the blood outlet and the gas exchanger, as is usual in heart-lung machines, can be intentionally omitted, since the atraumatic overall structure and the pulsatile pumping of the blood prevents the formation of emboli so that retardation of these is not necessary. The blood inlet and outlet lines are preferably embodied as cannula or tube connections, to be able to directly connect corresponding cannulas for connection to the patient, and therefore to keep the tubes as short as possible.

Such an arrangement creates a system for extracorporeal membrane oxygenation which is easily transportable as a compact unit and can be deployed quickly. The structure allows it to operate with a small number of short supply lines, with the risk of a blood clot on the surfaces of blood supply lines being further reduced. It is therefore proposed that the blood inlet line and the blood outlet line each have a length of 80 cm or less as a connection to a patient. The system operates independent of location and requires no special mountings. Non-fixed operation directly on the patient is also possible.

It is advantageous if a blood inlet line arranged on the housing and a blood outlet line arranged on the housing are oriented in the same direction. This means that be particularly short cannulas can be used and the housing can be arranged as close as possible to the patient.

A further reduction in the length of the cannulas can be achieved by arranging a blood outlet line and a blood inlet line on the same side of the housing.

A particularly compact structure is achieved by having the pulsatile blood pump act in an axial alignment of the gas exchanger.

As the preferred design variant, the pulsatile blood pump is arranged radially inside the gas exchanger.

Cumulatively or alternatively, the pulsatile blood pump can be arranged on a front face of the gas exchanger.

Pulsatile blood pumps, or blood pumps working according to the pulsatile principle, are pumps which work according to the positive displacement principle. In the filling phase the blood passes through the passive opening inlet valve and enters the expanding pump chamber. In the ejection phase the volume in the pump chamber is compressed and the blood is ejected through the outlet valve, which is also passive opening.

According to a particularly important aspect of the invention, which is essential to the invention independently of the other features of the invention, it is proposed that the pulsatile blood pump is driven pneumatically. The pulsatile blood pump can be driven with a plunger which acts on a piston in a cylinder, or which acts on a diaphragm. However, it is advantageous if the blood pump is driven with a pulsatile gas flow. This avoids the use of electrical components. This enables the entire arrangement to operate without, or with only a minimal supply of electrical power.

It is particularly advantageous if the pulsatile blood pump and the gas exchanger are connected to the same gas source. This enables the pressurized gas required for the gas exchanger to be used as a driving gas for the blood pump as well. This aspect of the invention is also essential to the invention, independently of the other features of the invention.

If the gas exchanger is connected via a valve to a pulsatile compressed gas supply, one line with pulsatile compressed gas is sufficient to supply the arrangement with gas for the gas exchanger and drive gas for the pump. Either the gas outlet of the pulsatile blood pump or of the pulsatile pump drive can be connected to the gas exchanger.

According to a particularly important aspect of the invention, which is also essential to the invention independently of the other features of the invention, it is proposed that the pulsatile blood pump is implemented as a balloon pump. It has a balloon and an inlet and an outlet valve. A flexible balloon is simple and inexpensive to manufacture and also shows a high level of failure reliability over numerous load cycles.

According to a further particularly important aspect of the invention, which is also essential to the invention independently of the other features of the invention, it is proposed that the pulsatile blood pump is embodied as a diaphragm pump, the diaphragm of which is pre-tensioned such that its passive position is that having the maximum filling of the pump. Accordingly, the positive displacement pump is embodied by a pre-tensioned diaphragm. This must allow the greatest filling of the pump chamber in its initial position, i.e. without driving pressure or force due to a plunger. The pump can therefore be operated by positive pressure. A negative pressure, which is otherwise standard, is not required.

A compact structure arises if a positive displacement pump is surrounded by bundles of membrane fibers.

The balloon of the pump is preferably pneumatically driven, while the membrane can be driven pneumatically or mechanically.

An advantageous arrangement comprises the inlet, inlet valve, pump chamber, outlet valve, gas exchanger fibers and outlet in the flow direction. Alternatively, an arrangement in the flow direction of inlet, inlet valve, pump chamber, gas exchanger fibers, outlet valve and outlet is proposed. Thus the gas exchange process can be improved where appropriate by applying increasing pressures.

An advantageous design variant is formed by an ECMO system with a centrally arranged balloon pump, in which an annular fiber bundle is radially permeated. The annular fiber bundle can be radially permeated with a length-to-diameter ratio less than or greater than or equal to 1:1.

An alternative embodiment provides a diaphragm pump mounted on an end face and a barrel-shaped fiber bundle which is diagonally permeated. This barrel-shaped fiber bundle can be diagonally permeated with a length-to-diameter ratio of less than or equal to or greater than 1:1.

Instead of a centrally arranged balloon pump, an end-face mounted diaphragm pump can also be provided.

The gas exchanger unit can be barrel shaped, square and/or flat. Suitable valves are ball valves, conical valves, disk valves or diaphragm valves.

Figure 2:
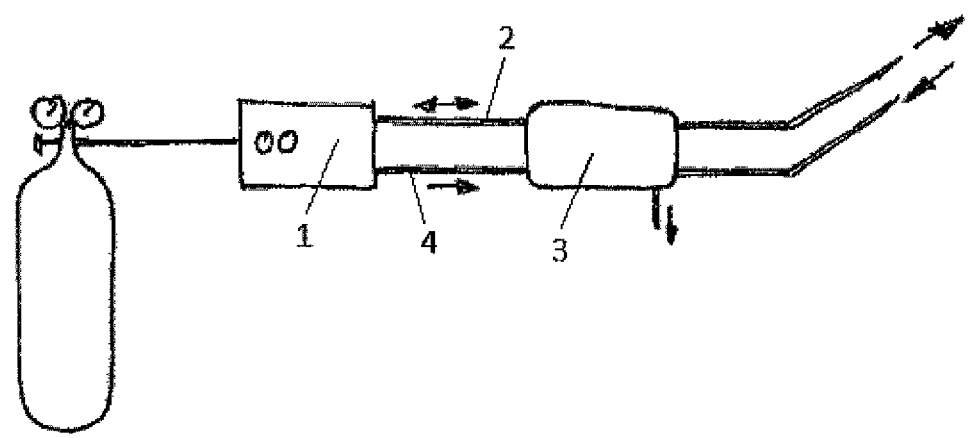
Figure 3:
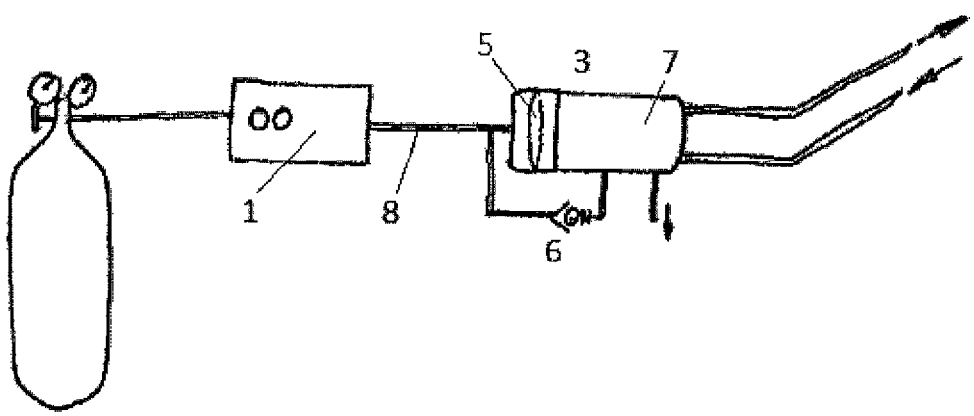
Figure 4:
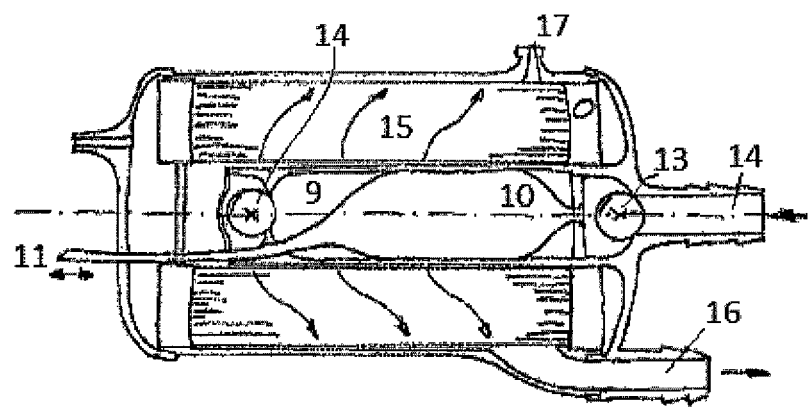
Figure 5:
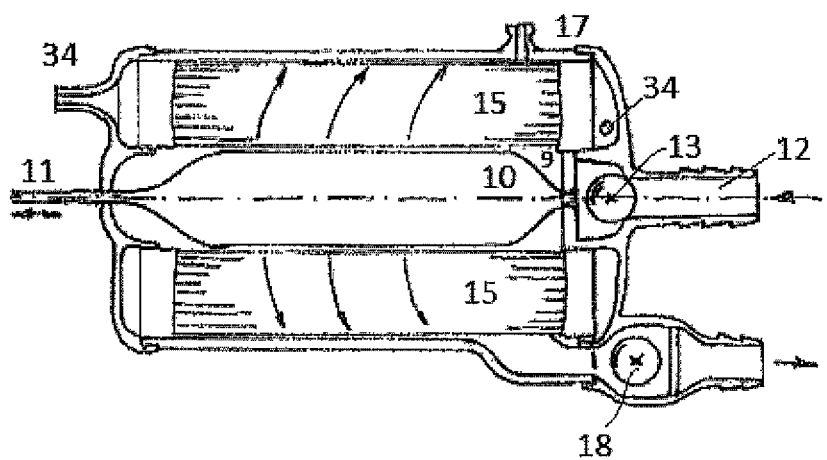
Figure 6:
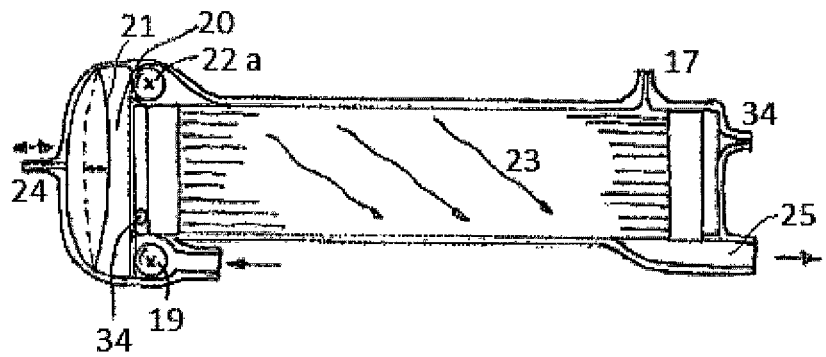
Figure 7:
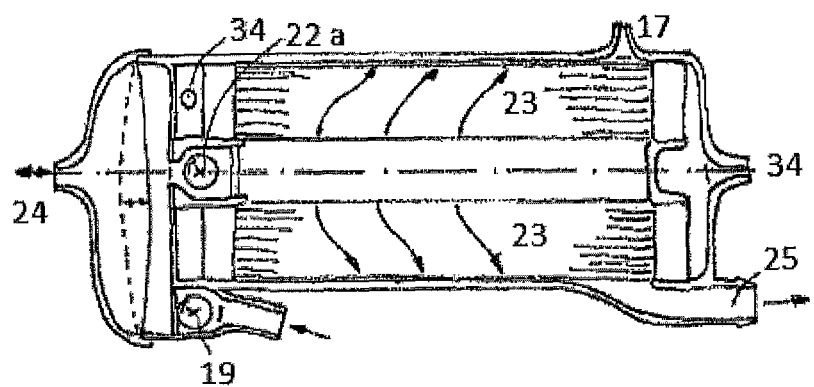
Figure 8:
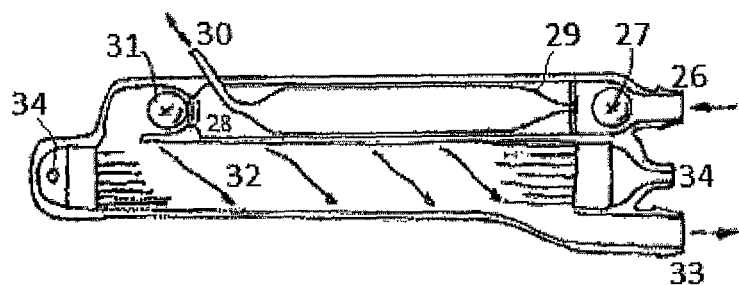
Figure 9:
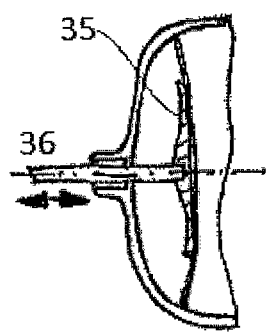

Different arrangements according to the invention are shown in the figures, which serve as exemplary embodiments. Shown are:

FIG. 1 an ECMO system consisting of a drive console and patient system with bypass for supplying the oxygenator, FIG. 2 an arrangement in accordance with FIG. 1 with two lines between drive console and patient system, FIG. 3 an arrangement with a pressure relief valve between drive console and patient system, FIG. 4 a housing with a radially internal balloon and two radially internal valves, FIG. 5 a housing in accordance with FIG. 4 with only one radially internal valve, FIG. 6 a housing with barrel-shaped gas exchanger fibers and a blood pump arranged on an end face, FIG. 7 a housing with annularly arranged gas exchanger fibers and a blood pump arranged on an end face, FIG. 8 a housing in which the blood pump and gas exchanger are arranged side by side in parallel, and FIG. 9 a system with a mechanically powered pump.

The basis of the invention is an ECMO system, which pumps the blood with a positive displacement pump and in which the drive power is released by the compressed respiration gas. In this arrangement the gas is fed to a pneumatically operating drive console 1. The console generates an alternating rising and falling pressure, which is fed via a line 2 to the pump of the patient system 3 (FIG. 1).

After the gas has passed through the console, instead of being passed to the environment it can be fed to the oxygenator of the patient system via a separate line 4 (FIG. 2). A more effective utilization of the gas is therefore obtained.

Furthermore, a solution is proposed in which, as described, a rising and falling pressure is fed to the pump and on the patient system 3 a pressure relief valve 6 is connected in parallel with the pump 5, which is connected on the other side to the gas exchanger or oxygenator 7 of the patient system, and which at the same time supplies this with respiration gas at the upper pressure level (FIG. 3), There is therefore only one supply line 8 to the patient system.

As described above, a pulsatile blood pump is combined with an oxygenator in a compact unit, the patient system. The following schemes are proposed for this purpose.

In one scheme (FIG. 4) a balloon 10 is located in the pump chamber 9, which is centrally arranged, and this balloon 10 is pressurized and relaxed with compressed air in a pulsatile manner with a connecting hose 11. The blood passes from the patient via a nozzle 12 and a valve 13 to reach the pumping chamber 9. Through a second valve 14 the blood reaches the gas exchanger fibers 15, which can be arranged in an annular pattern. These are radially permeated and the blood thus reaches the outlet 16. Opposite the outlet 16 a ventilation port 17 is provided, to simplify the filling and bleeding of the system.

In an alternative arrangement (FIG. 5), the second valve 18 is located behind the gas exchanger fibers in the flow direction.

In a further scheme (FIG. 6) the blood passes through a valve 19 into a pump chamber 20 which is bounded on one side by a flexible diaphragm 21, and through a second valve 22a to the gas exchanger fibers 23. The membrane is connected on the other side to a connecting hose 24 and via this it is pressurized and relaxed with compressed air by the drive assembly in a pulsatile manner. The gas exchanger fibers 23 can be in a barrel-shaped (FIG. 6) or annular (FIG. 7) arrangement. While in the barrel-shaped arrangement the valve 22a is seated externally, in the annular arrangement is arranged centrally 22a. After the blood flows through the oxygenation region, diagonally in the barrel-shaped fiber arrangement or radially in the annular arrangement, it reaches the outlet 25, positioned low down, and from there passes back to the patient. When filling the system a ventilation port 17 near the outlet is useful. This is applied at the highest point of the system.

In a further scheme (FIG. 8) the pump unit and the gas exchanger unit are arranged in parallel. The blood passes through a nozzle 26 and 27 via a valve into the pump chamber 28, in which a balloon 29 is located. This is pressurized with compressed air and relaxed in a pulsatile manner via the supply line 30. Through an additional valve 31 the blood reaches the gas exchanger fibers 32 and from there passes back to the patient via the outlet nozzle 33.

In all solutions the gas exchanger fibers are supplied with respiration gas and the respiration gas is discharged via an inlet and outlet line 34.

Is conceivable that, in the solutions with the diaphragm (FIGS. 6 and 7), these are mechanically driven by a pressure plate 35 and a plunger 36 (FIG. 9). For this purpose a drive console with a suitable actuator is used. This actuator can also be pneumatic.

Various valve geometries are proposed for the solutions described. This means that the invention can be implemented with ball valves as shown. Conical valves, disk valves or diaphragm valves are also conceivable, however.

By various geometric arrangements of the pump chambers, valves, design of the valves and oxygenator fibers in combination with both schemes, different designs emerge which facilitate an extremely compact ECMO system.

It is proposed to configure the blood inlet and outlet lines in one geometric direction, in order to simplify the connection to the patient and to keep the connection cannulas as short as possible.

It is proposed to produce, deliver and store the system optionally already filled, so that it is quickly ready for use.

The pulsatile blood pumping has an advantageous effect on the gas exchange in the oxygenator and the elution of the whole system by a continuous mixing of the blood, and an improved elution of critical areas. Thus, the formation of thrombi is counteracted.

Both functional principles, in addition to the gas exchanger can also be combined with a heat exchanger.

Since the pump energy is transferred via only one gas connection (with the exception of the last solution) and not mechanically via an electric motor connected to the system as is current practice, the system can be positioned more flexibly and closer to, or on, the patient.

This results in different options for driving the pulsatile pump, which makes the device combination and usage more flexible.

Since oxygen for the gas exchange in the oxygenator is available in compressed form in gas cylinders or via a centralized supply line, this gas pressure can be used to also facilitate the pulsatile drive using a suitable pneumatic circuit. No additional energy source is thus required, which facilitates a more compact, simpler and less expensive drive.

The invention claimed is:

1. An arrangement comprising:
   a rigid housing having a blood inlet, a blood outlet, a pulsatile gas inlet, and an oxygenation gas inlet;
   a pulsatile blood pump within the housing and comprising an expandable member connected to receive pulsatile gas from the pulsatile gas inlet;
   a gas exchanger for extracorporeal membrane oxygenation within the housing;
   a gas source external to the housing and having at least a pulsatile gas outlet;
   wherein the pulsatile blood pump is arranged to deliver blood from the blood inlet to the gas exchanger, wherein the pulsatile gas inlet is connected to receive pulsatile gas from the pulsatile gas outlet of the external gas source to provide pumping power to the expandable member of said pulsatile blood pump, and wherein a portion of the gas from the gas source is fed to said gas exchanger to provide an oxygenation function.

2. The arrangement according to claim 1, further comprising a blood inlet line connected to the blood inlet on the housing and a blood outlet line connected to the blood inlet on the housing, wherein each of the blood inlet line and the blood outlet line include cannulas or tube connections configured to access a patient's blood vessels.

3. The arrangement according to claim 2, wherein the blood inlet line and a blood outlet line each have a length of 80 cm or less.

4. The arrangement according to claim 2, wherein the blood inlet and the blood outlet are arranged on the housing so that the blood inlet line and the blood outlet line are oriented in the same direction.

5. The arrangement according to claim 2, wherein the blood inlet and the blood outlet are disposed on the same end of the housing.

6. The arrangement according to claim 2, wherein the blood inlet and the blood outlet are disposed on opposite ends of the housing.

7. The arrangement according to claim 1, further comprising:
   a high pressure valve disposed to receive gas from the pulsatile gas outlet of the gas source, such that when a pressure of the pulsatile gas outlet exceeds a preset value, gas is provided to said gas exchanger.

8. The arrangement according to claim 1, wherein the pulsatile blood pump is axially aligned with the gas exchanger.

9. The arrangement according to claim 6, wherein the pulsatile blood pump is coaxially aligned inside the gas exchanger.

10. The arrangement according to claim 1, wherein the pulsatile blood pump is disposed on an end face of the gas exchanger and the expandable member comprises a flexible diaphragm.

11. The arrangement according to claim 1, wherein the pulsatile gas outlet of the gas source provides gas under pressure to both said blood pump and said gas exchanger.

12. The arrangement according to claim 1, wherein the expandable member of the pulsatile blood pump comprises a balloon.

13. The arrangement according to claim 1, wherein the expandable member of the pulsatile blood pump comprises a diaphragm which is pre-tensioned such that its passive position is that having the maximum filling of the pump.

14. The arrangement according to claim 1, wherein the gas exchanger is connected via a valve to the pulsatile gas outlet of the gas source.

15. The arrangement as in claim 1, wherein after the gas has been delivered from the gas source to the expandable member, instead of being passed to the environment, the gas is fed to the oxygenator in a separate line to obtain a more effective utilization of the gas.

16. The arrangement as in claim 1, wherein the gas source comprises a pneumatically operated gas console connected to a gas cylinder.

17. The arrangement as in claim 16, wherein the pulsatile gas inlet is connected to the pneumatically operated gas console and the oxygenation gas inlet is connected to the gas cylinder.

18. The arrangement as in claim 16, wherein the pulsatile gas inlet and the oxygenation gas inlet are connected to the pneumatically operated gas console.

19. The arrangement as in claim 1, wherein the gas source comprises a pneumatically operated gas console connected to a centralized supply line.

* * * * *